(12) United States Patent
Housman et al.

(10) Patent No.: US 9,949,820 B2
(45) Date of Patent: Apr. 24, 2018

(54) COMPOSITE INTERFERENCE SCREWS AND DRIVERS

(71) Applicant: Smith & Nephew, Inc., Memphis, TN (US)

(72) Inventors: Mark Edwin Housman, North Attleborough, MA (US); Paul Steven Vincuilla, Brockton, MA (US); Peter James Cashmore, Pawtucket, RI (US); Rebecca Ann Blough, West Warwick, RI (US); Wei Li Fan, Boston, MA (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 15/484,319

(22) Filed: Apr. 11, 2017

(65) Prior Publication Data

US 2017/0216017 A1 Aug. 3, 2017

Related U.S. Application Data

(63) Continuation of application No. 14/670,794, filed on Mar. 27, 2015, which is a continuation of application
(Continued)

(51) Int. Cl.
*A61B 17/88* (2006.01)
*A61F 2/08* (2006.01)
(Continued)

(52) U.S. Cl.
CPC ........ *A61F 2/0811* (2013.01); *A61B 17/0401* (2013.01); *A61B 17/864* (2013.01);
(Continued)

(58) Field of Classification Search
CPC ........................ A61B 17/8875; A61B 17/8888
See application file for complete search history.

(56) References Cited

U.S. PATENT DOCUMENTS 4,463,788 A * 8/1984 Corona ................. B25G 1/085
81/177.4
4,961,740 A 10/1990 Ray et al.
(Continued)

FOREIGN PATENT DOCUMENTS

JP 2008132327 6/2008

OTHER PUBLICATIONS

Japanese Office Action from corresponding International Application No. 2015-561605, dated Dec. 25, 2017.
(Continued)

*Primary Examiner* — Nicholas Woodall
(74) *Attorney, Agent, or Firm* — Burns & Levinson, LLP; Joseph M. Maraia

(57) ABSTRACT

The present disclosure relates to a delivery device and screw combination. The combination includes a delivery device comprising a handle and a shaft coupled to the handle, the shaft including a proximal end, a distal end, a non-circular cannulation, and markings along a length of the shaft; an interference screw coupled to the delivery device comprising a proximal end and a distal end, the screw including threads extending in an open helical form from the proximal end to the distal end, a suture bridge located at a distal end of the screw and housed within a slot of the delivery device shaft, and a plurality of runners extending longitudinally along an interior of the screw, the runners housed within grooves of the delivery device shaft; and a suture disposed around the suture bridge, ends of the suture extending through the cannulation of the delivery device shaft.

7 Claims, 22 Drawing Sheets

Related U.S. Application Data

No. 13/418,223, filed on Mar. 12, 2012, now Pat. No. 9,308,080, said application No. 14/670,794 is a continuation-in-part of application No. 13/044,777, filed on Mar. 10, 2011, now Pat. No. 8,979,865.

(60) Provisional application No. 61/451,736, filed on Mar. 11, 2011, provisional application No. 61/451,731, filed on Mar. 11, 2011, provisional application No. 61/451,644, filed on Mar. 11, 2011, provisional application No. 61/451,743, filed on Mar. 11, 2011, provisional application No. 61/659,080, filed on Jun. 28, 2010, provisional application No. 61/334,808, filed on May 14, 2010, provisional application No. 61/312,291, filed on Mar. 10, 2010.

(51) Int. Cl.
*A61B 17/04* (2006.01)
*A61B 17/86* (2006.01)

(52) U.S. Cl.
CPC ...... *A61B 17/8645* (2013.01); *A61B 17/8875* (2013.01); *A61B 17/8888* (2013.01); *A61B 2017/0409* (2013.01); *A61B 2017/0441* (2013.01); *A61F 2002/087* (2013.01); *A61F 2002/0858* (2013.01); *A61F 2002/0888* (2013.01)

(56) References Cited

U.S. PATENT DOCUMENTS

| | | | |
|---|---|---|---|
| 5,026,373 A | | 6/1991 | Ray et al. |
| 5,055,104 A | | 10/1991 | Ray |
| 5,354,299 A | * | 10/1994 | Coleman ............ A61B 17/1615 606/916 |
| 5,695,497 A | | 12/1997 | Stahelin |
| 5,968,098 A | | 10/1999 | Winslow |
| 6,216,348 B1 | * | 4/2001 | Martirossian ............ B26B 1/10 30/329 |
| 6,283,973 B1 | * | 9/2001 | Hubbard ............ A61B 17/8615 411/393 |
| 6,503,251 B1 | | 1/2003 | Shadduck |
| 6,527,774 B2 | | 3/2003 | Lieberman |
| 6,685,728 B2 | | 2/2004 | Sinnott et al. |
| 7,883,529 B2 | | 2/2011 | Sinnott et al. |
| 7,914,539 B2 | | 3/2011 | Stone et al. |
| 8,034,090 B2 | | 10/2011 | Stone et al. |
| 8,167,906 B2 | | 5/2012 | Cauldwell et al. |
| 8,597,328 B2 | | 12/2013 | Cauldwell et al. |
| 8,979,865 B2 | | 3/2015 | Fan et al. |
| 9,155,531 B2 | | 10/2015 | Housman |
| 9,308,080 B2 | | 4/2016 | Housman et al. |
| 9,393,006 B2 | | 7/2016 | Housman et al. |
| 9,427,270 B2 | | 8/2016 | Housman |
| 9,526,488 B2 | | 12/2016 | Arai et al. |
| 9,579,188 B2 | | 2/2017 | Bowman et al. |
| 2002/0055742 A1 | | 5/2002 | Lieberman |
| 2004/0093032 A1 | | 5/2004 | Sinnott et al. |
| 2005/0075680 A1 | * | 4/2005 | Lowry ............ A61N 1/0531 607/45 |
| 2005/0222681 A1 | | 10/2005 | Richley et al. |
| 2006/0030948 A1 | | 2/2006 | Manrique et al. |
| 2006/0100627 A1 | | 5/2006 | Stone et al. |
| 2008/0179839 A1 | * | 7/2008 | Walters ............ B23B 31/008 279/51 |
| 2009/0076544 A1 | | 3/2009 | DiMatteo et al. |
| 2009/0319043 A1 | * | 12/2009 | McDevitt ............ A61B 17/809 623/13.14 |
| 2011/0054526 A1 | | 3/2011 | Stone et al. |
| 2011/0224727 A1 | | 9/2011 | Housman et al. |
| 2012/0179163 A1 | | 7/2012 | Housman et al. |
| 2013/0178901 A1 | | 7/2013 | Arai et al. |
| 2014/0081339 A1 | | 3/2014 | Bowman et al. |
| 2014/0172016 A1 | | 6/2014 | Housman |
| 2014/0277129 A1 | | 9/2014 | Arai et al. |
| 2014/0277192 A1 | | 9/2014 | Housman |
| 2015/0196388 A1 | | 7/2015 | Housman et al. |
| 2015/0327984 A1 | | 11/2015 | Arai et al. |
| 2016/0235399 A1 | | 8/2016 | Housman et al. |
| 2016/0374661 A1 | | 12/2016 | Housman et al. |
| 2017/0014224 A1 | | 1/2017 | Arai et al. |
| 2017/0020589 A1 | | 1/2017 | Bowman et al. |
| 2017/0049438 A1 | | 2/2017 | Arai et al. |

OTHER PUBLICATIONS

Chinese Decision on Rejection from corresponding International Application No. 201480012203.0, dated Dec. 14, 2017.

* cited by examiner

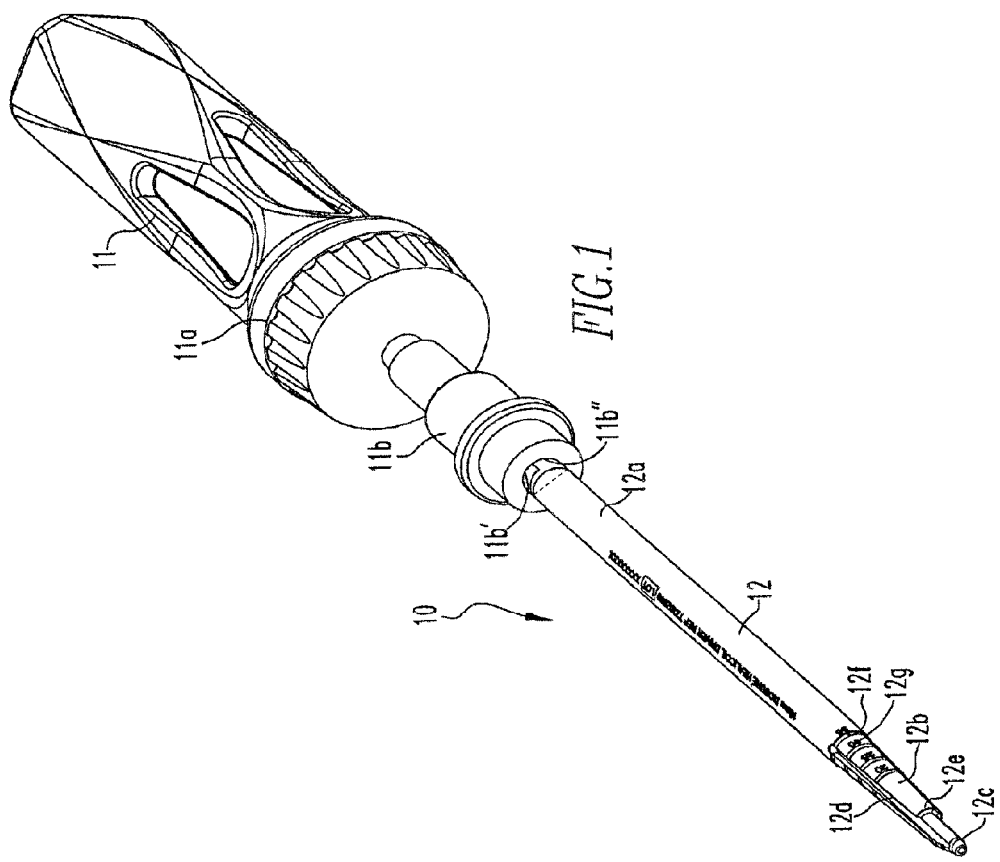

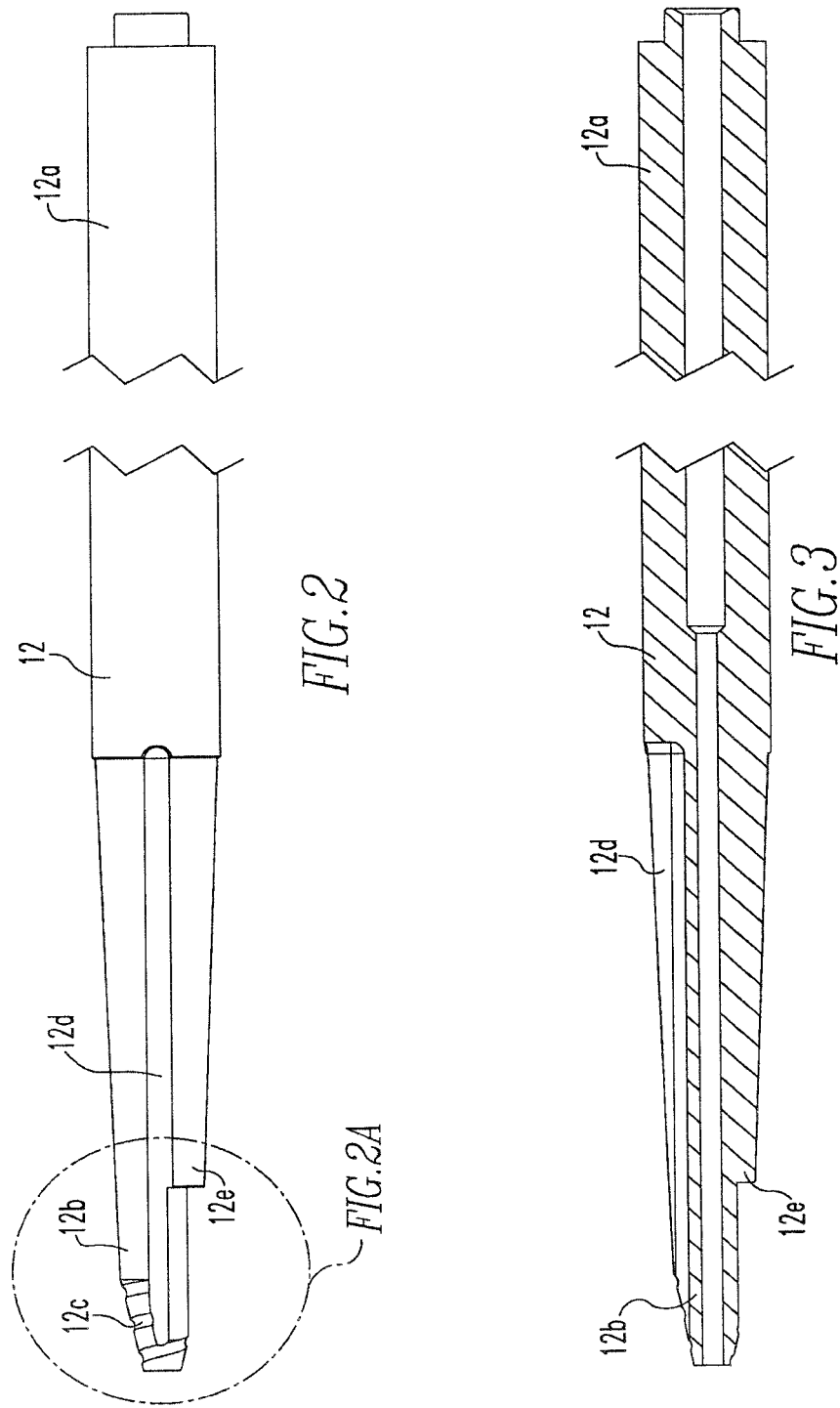

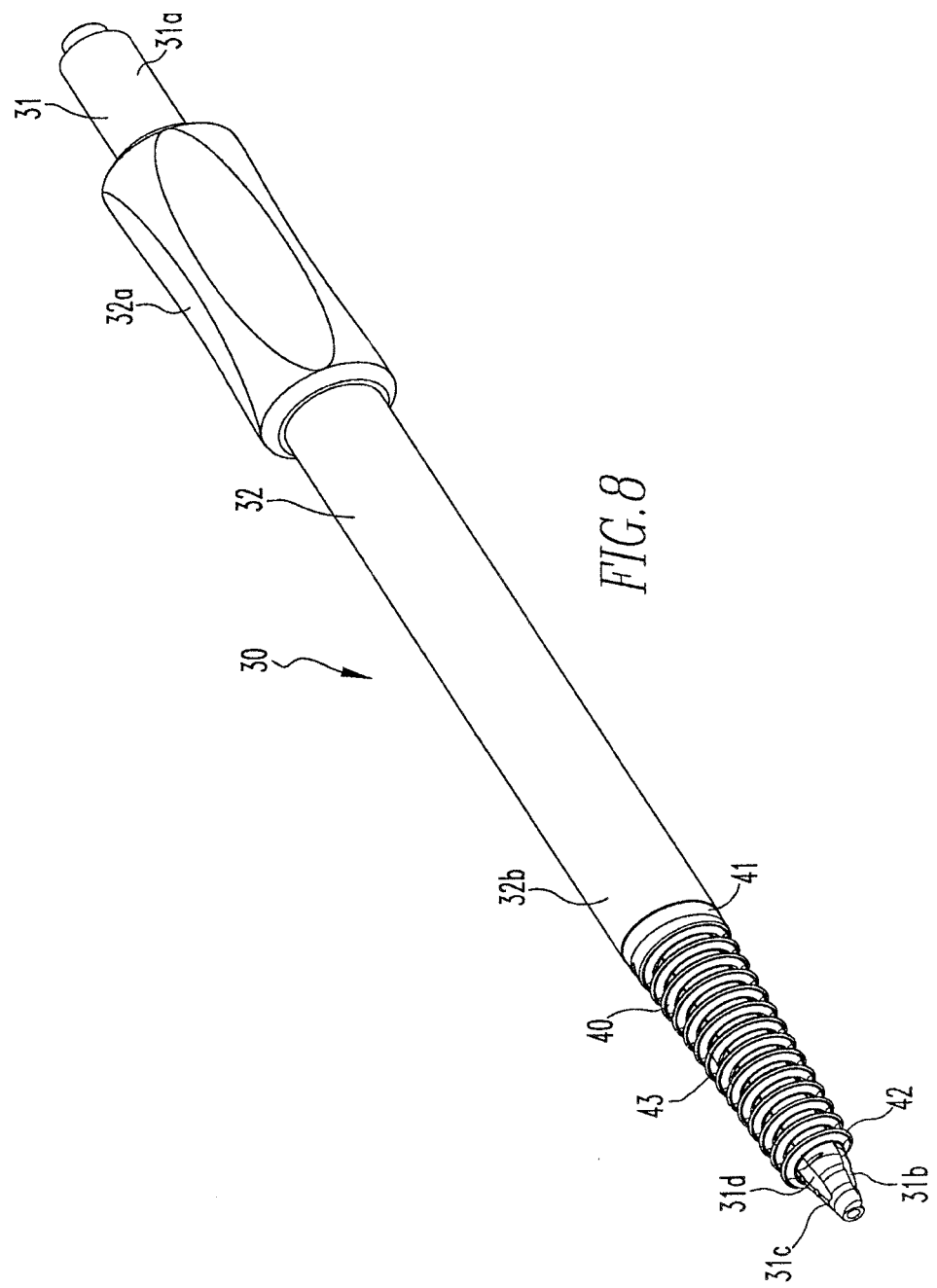

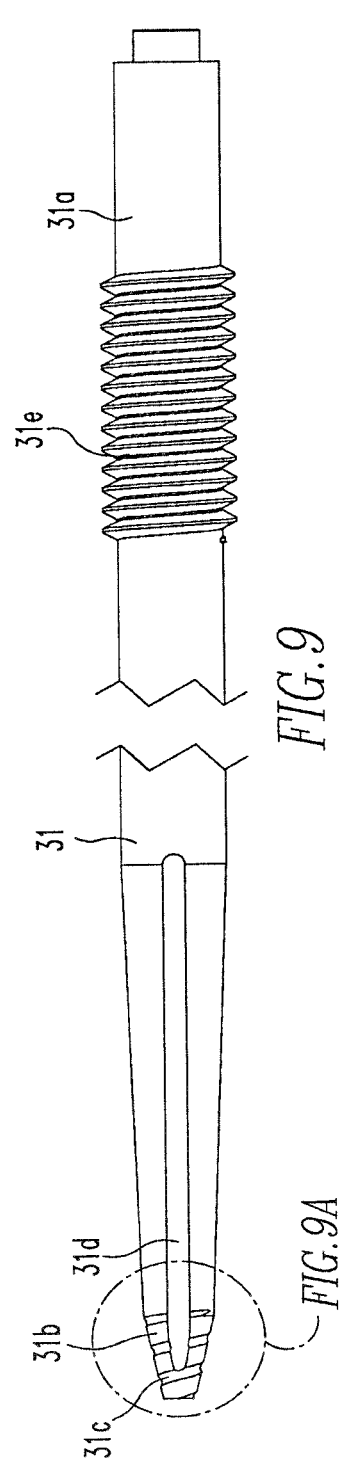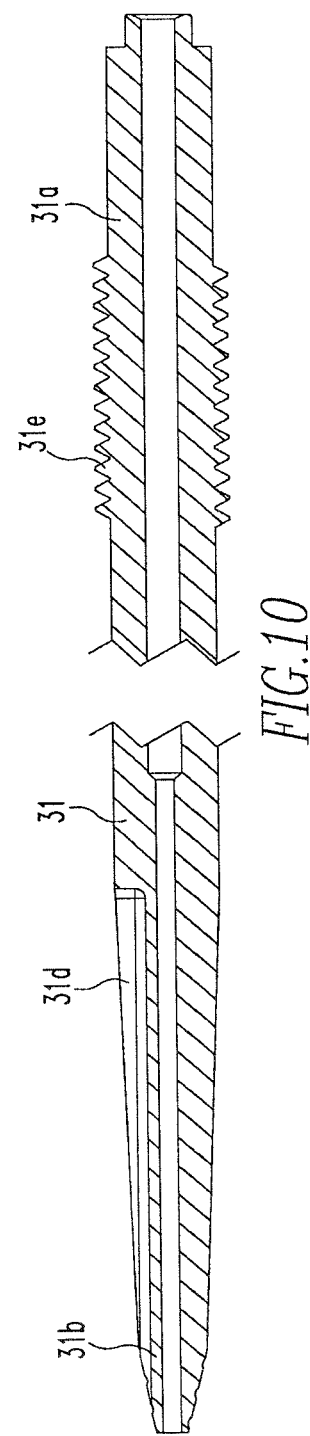

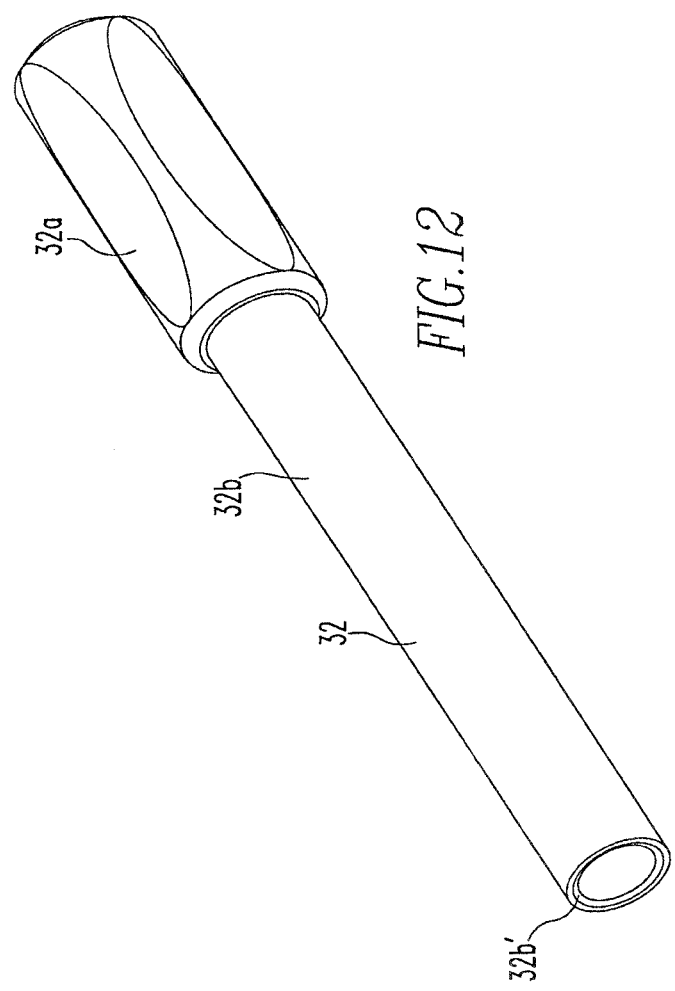
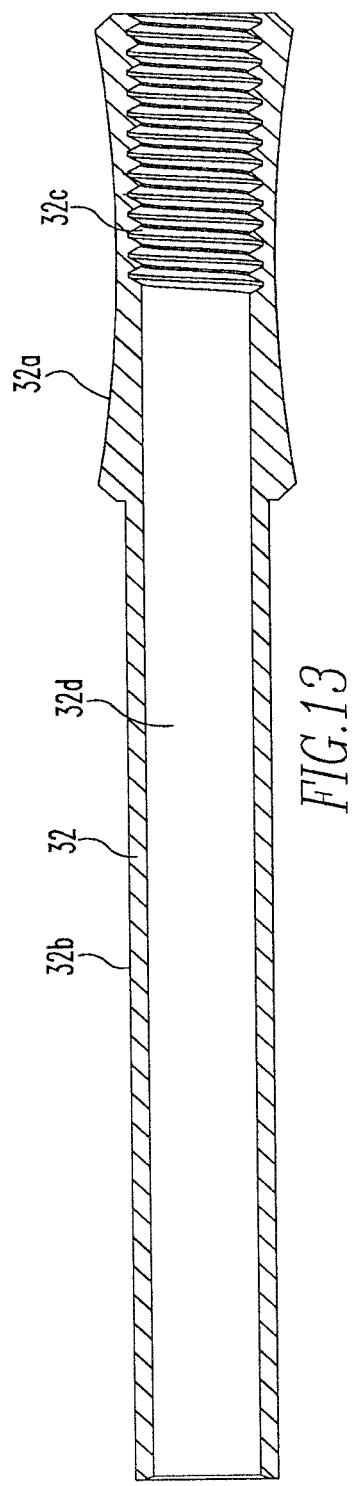

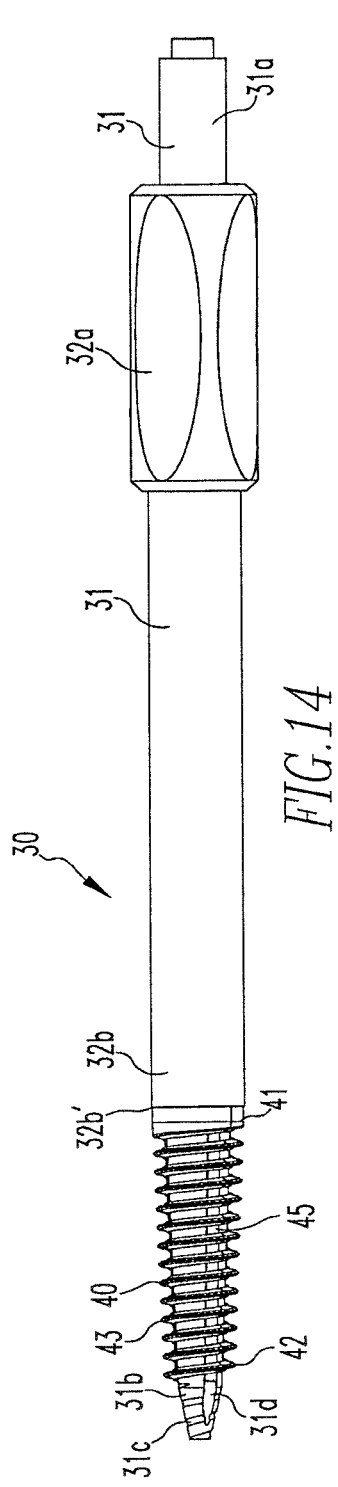
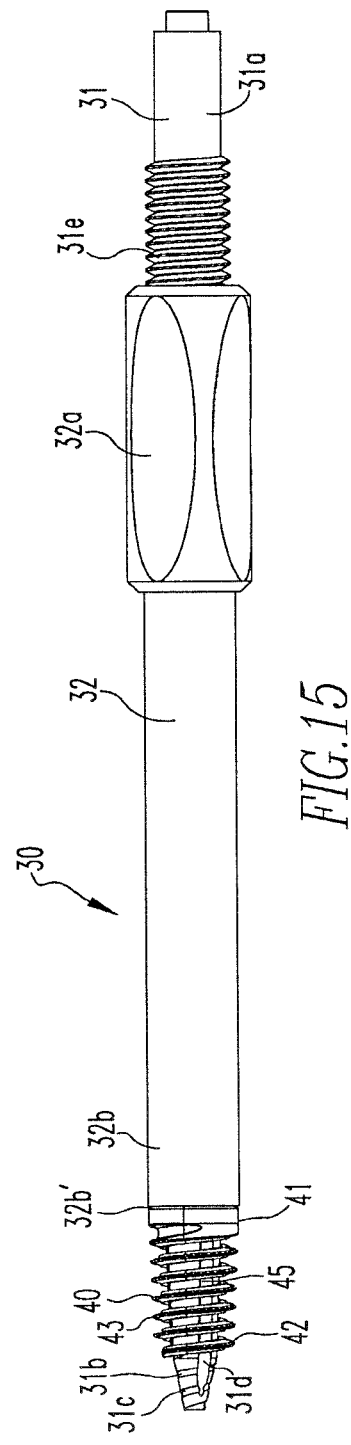

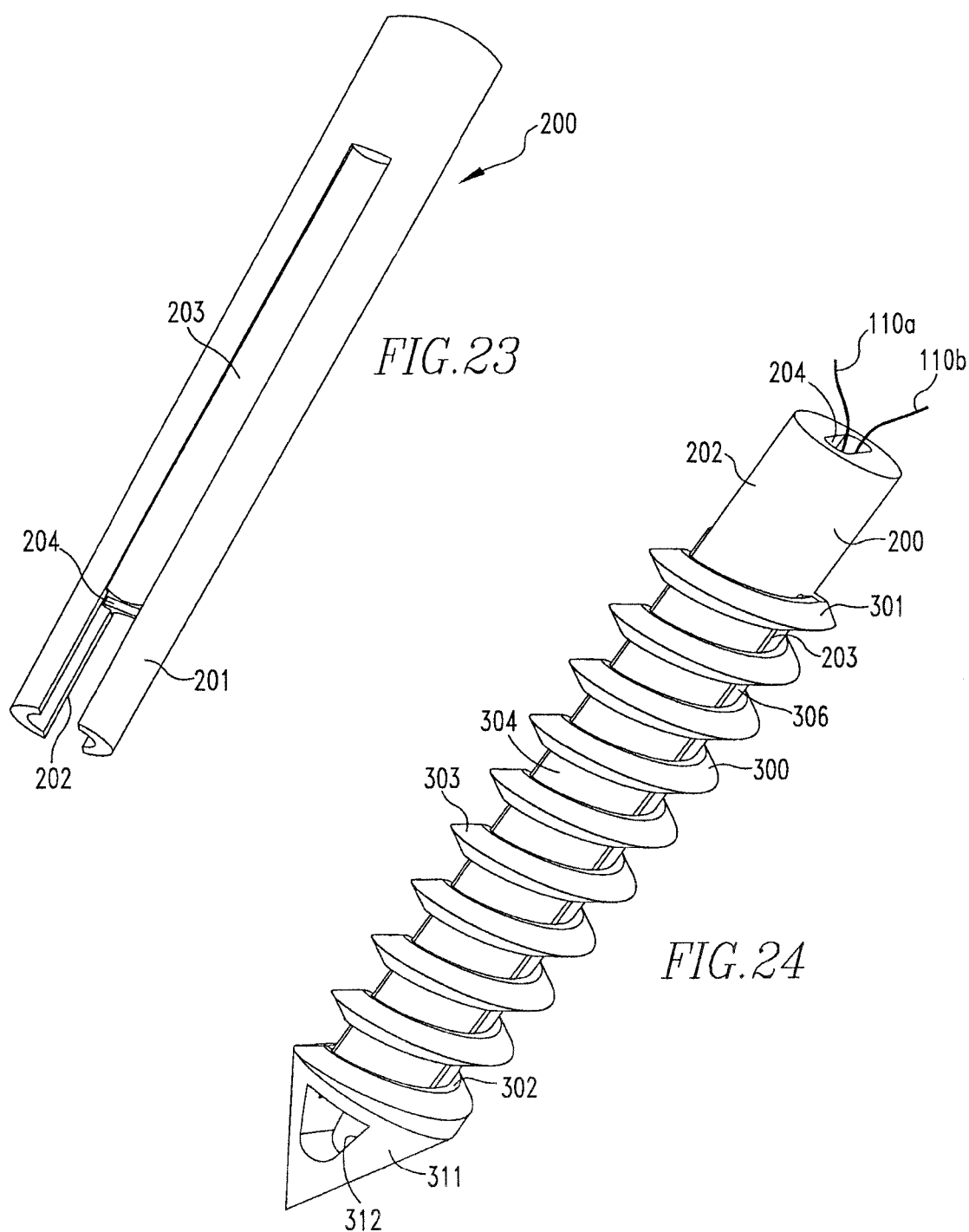

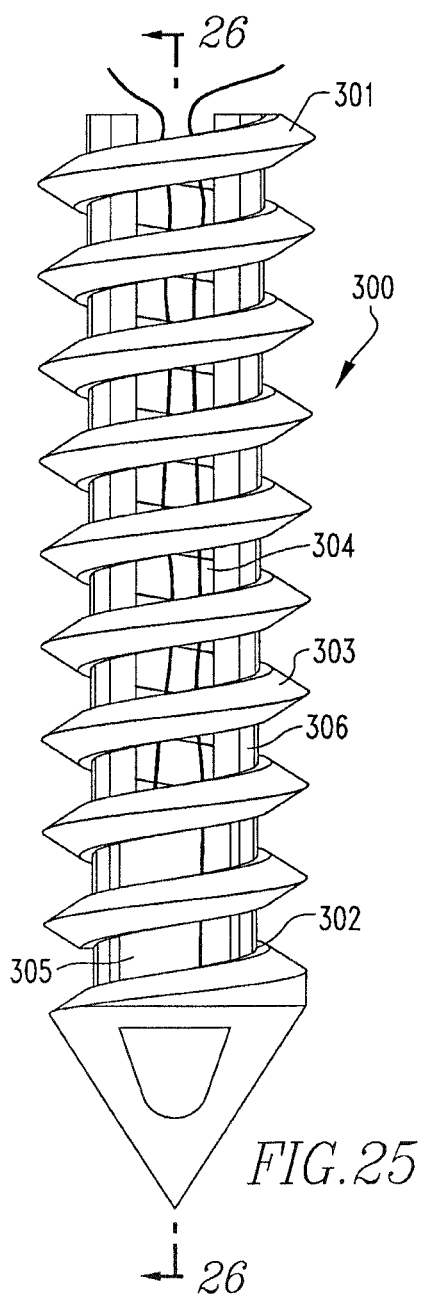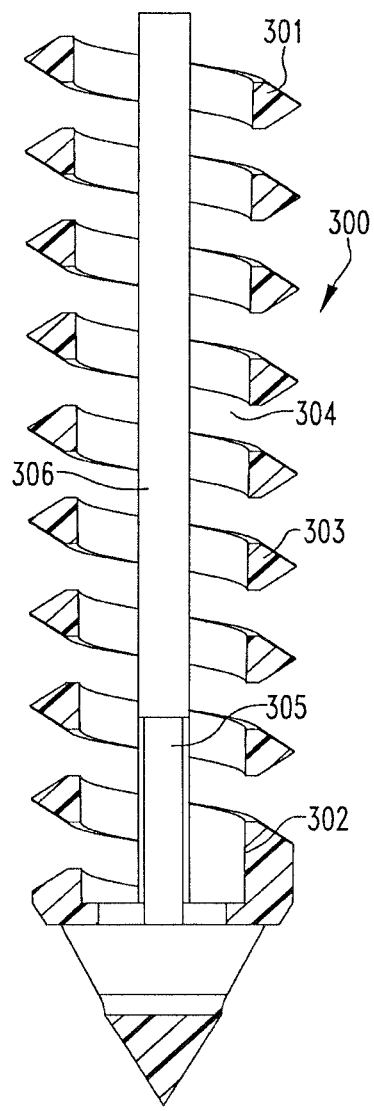
FIG.25
FIG.26

COMPOSITE INTERFERENCE SCREWS AND DRIVERS

CROSS-REFERENCE TO RELATED APPLICATIONS

This application is a continuation of co-pending U.S. patent application Ser. No. 14/670,794, filed on Mar. 27, 2015, entitled COMPOSITE INTERFERENCE SCREWS AND DRIVERS, which in turn is a continuation of U.S. patent application Ser. No. 13/418,223, filed on Mar. 12, 2012, which in turn claims priority to and benefit of U.S. Patent Application Ser. No. 61/451,644, filed on Mar. 11, 2011, U.S. Patent Application Ser. No. 61/451,731, filed on Mar. 11, 2011, U.S. Patent Application Ser. No. 61/451,736, filed Mar. 11, 2011, and U.S. Patent Application Ser. No. 61/451,743, filed on Mar. 11, 2011, and which is also a continuation-in-part of U.S. patent application Ser. No. 13/044,777, filed on Mar. 10, 2011, which in turn claims priority to and benefit of U.S. Patent Application Ser. No. 61/312,291, filed on Mar. 10, 2010, U.S. Patent Application Ser. No. 61/334,808, filed on May 14, 2010, and U.S. Patent Application Ser. No. 61/359,080, filed on Jun. 28, 2010, the disclosures of which are incorporated herein by reference in their entireties for all purposes.

BACKGROUND

Field of Technology

The present disclosure relates to medical apparatuses and procedures in general, and more particularly to medical apparatuses and procedures for reconstructing a ligament.

Related Art

In many cases, ligaments are torn or ruptured as the result of an accident. Accordingly, various procedures have been developed to repair or replace such damaged ligaments.

For example, in the human knee, the anterior and posterior cruciate ligaments (i.e., the "ACL" and "PCL") extend between the top end of the tibia and the bottom end of the femur. Often, the anterior cruciate ligament (i.e., the ACL) is ruptured or torn as the result of, for example, a sports-related injury. Consequently, various surgical procedures have been developed for reconstructing the ACL so as to restore substantially normal function to the knee.

In many instances, the ACL may be reconstructed by replacing the ruptured ACL with a graft ligament. More particularly, in such a procedure, bone tunnels are generally formed in both the top of the tibia and the bottom of the femur, with one end of the graft ligament being positioned in the femoral tunnel and the other end of the graft ligament being positioned in the tibial tunnel, and with the intermediate portion of the graft ligament spanning the distance between the bottom of the femur and the top of the tibia. The two ends of the graft ligament are anchored in their respective bone tunnels in various ways well known in the art so that the graft ligament extends between the bottom end of the femur and the top end of the tibia in substantially the same way, and with substantially the same function, as the original ACL. This graft ligament then cooperates with the surrounding anatomical structures so as to restore substantially normal function to the knee.

In some circumstances, the graft ligament may be a ligament or tendon which is harvested from elsewhere within the patient's body, e.g., a patella tendon with or without bone blocks attached, a semitendinosus tendon and/or a gracilis tendon.

As noted above, various approaches are well known in the art for anchoring the two ends of the graft ligament in the femoral and tibial bone tunnels.

In one well-known procedure, which may be applied to femoral fixation, tibial fixation, or both, the end of the graft ligament is placed in the bone tunnel, and then the graft ligament is fixed in place using a headless orthopedic screw, generally known in the art as an "interference" screw. More particularly, with this approach, the end of the graft ligament is placed in the bone tunnel and then the interference screw is advanced into the bone tunnel so that the interference screw extends parallel to the bone tunnel and simultaneously engages both the graft ligament and the side wall of the bone tunnel. In this arrangement, the interference screw essentially drives the graft ligament laterally, into engagement with the opposing side wall of the bone tunnel, whereby to secure the graft ligament to the host bone with a so-called "interference fit". Thereafter, over time (e.g., several months), the graft ligament and the host bone grow together at their points of contact so as to provide a strong, natural joinder between the ligament and the bone.

Interference screws have proven to be an effective means for securing a graft ligament in a bone tunnel. However, the interference screw itself generally takes up a substantial amount of space within the bone tunnel, which can limit the surface area contact established between the graft ligament and the side wall of the bone tunnel. This in turn limits the region of bone-to-ligament in-growth, and hence can affect the strength of the joinder. By way of example but not limitation, it has been estimated that the typical interference screw obstructs about 50% of the potential bone-to-ligament integration region.

For this reason, substantial efforts have been made to provide interference screws fabricated from absorbable materials, so that the interference screw can eventually disappear over time and bone-to-ligament in-growth can take place about the entire perimeter of the bone tunnel. To this end, various absorbable interference screws have been developed which are made from biocompatible, bioabsorbable polymers, e.g., polylactic acid (PLA), polyglycolic acid (PGA), etc. These polymers generally provide the substantial mechanical strength needed to advance the interference screw into position, and to thereafter hold the graft ligament in position while bone-to-ligament in-growth occurs, without remaining in position on a permanent basis.

In general, interference screws made from such biocompatible, bioabsorbable polymers have proven clinically successful. However, these absorbable interference screws still suffer from several disadvantages. First, clinical evidence suggests that the quality of the bone-to-ligament in-growth is somewhat different than natural bone-to-ligament in-growth, in the sense that the aforementioned bioabsorbable polymers tend to be replaced by a fibrous mass rather than a well-ordered tissue matrix. Second, clinical evidence suggests that absorption generally takes a substantial period of time, e.g., on the order of three years or so. Thus, during this absorption time, the bone-to-ligament in-growth is still significantly limited by the presence of the interference screw. Third, clinical evidence suggests that, for many patients, absorption is never complete, leaving a substantial foreign mass remaining within the body. This problem is exacerbated somewhat by the fact that absorbable interference screws generally tend to be fairly large in order to provide them with adequate strength, e.g., it is common for an interference screw to have a diameter (i.e., an outer diameter) of 8-12 mm and a length of 20-25 mm.

Thus, there is a need for a new and improved interference fixation system which (i) has the strength needed to hold the graft ligament in position while bone-to-ligament in-growth occurs, and (ii) promotes superior bone-to-ligament in-growth.

SUMMARY

In one aspect, the present disclosure relates to a delivery device and screw combination. The combination includes a delivery device comprising a handle and a shaft coupled to the handle, the shaft including a proximal end, a distal end, a non-circular cannulation, and markings along a length of the shaft; an interference screw coupled to the delivery device comprising a proximal end and a distal end, the screw including threads extending in an open helical form from the proximal end to the distal end, a suture bridge located at a distal end of the screw and housed within a slot of the delivery device shaft, and a plurality of runners extending longitudinally along an interior of the screw, the runners housed within grooves of the delivery device shaft; and a suture disposed around the suture bridge, ends of the suture extending through the cannulation of the delivery device shaft.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

BRIEF DESCRIPTION OF THE DRAWINGS

The accompanying drawings, which are incorporated in and form a part of the specification, illustrate the embodiments of the present disclosure and together with the written description serve to explain the principles, characteristics, and features of the disclosure. In the drawings:

FIG. 1 shows a first embodiment of the delivery device of the present disclosure.

FIG. 2 shows a side view of the shaft of the delivery device of FIG. 1.

FIG. 3 shows a cross-sectional view of the shaft of FIG. 2.

FIG. 8 shows a second embodiment of a shaft of the present disclosure.

FIG. 9 shows a side view of the inner member of the shaft of FIG. 8.

FIG. 10 shows a cross-sectional view of the inner member of the shaft of FIG. 9.

FIG. 12 shows an isometric view of the outer member of the shaft of FIG. 8.

FIG. 13 shows a cross-sectional view of the outer member of FIG. 12.

FIGS. 14 and 15 show side views of the shaft of FIG. 8 with the outer member in different positions.

FIG. 23 shows an isometric view of the shaft of FIG. 21.

FIG. 24 shows an isometric view of the shaft of FIG. 21 and an alternative screw for use with the shaft.

FIG. 25 shows a side view of the screw of FIG. 24.

FIG. 26 shows a cross-sectional view of the screw of FIG. 24.

DETAILED DESCRIPTION OF THE EMBODIMENTS

Figure 2A:
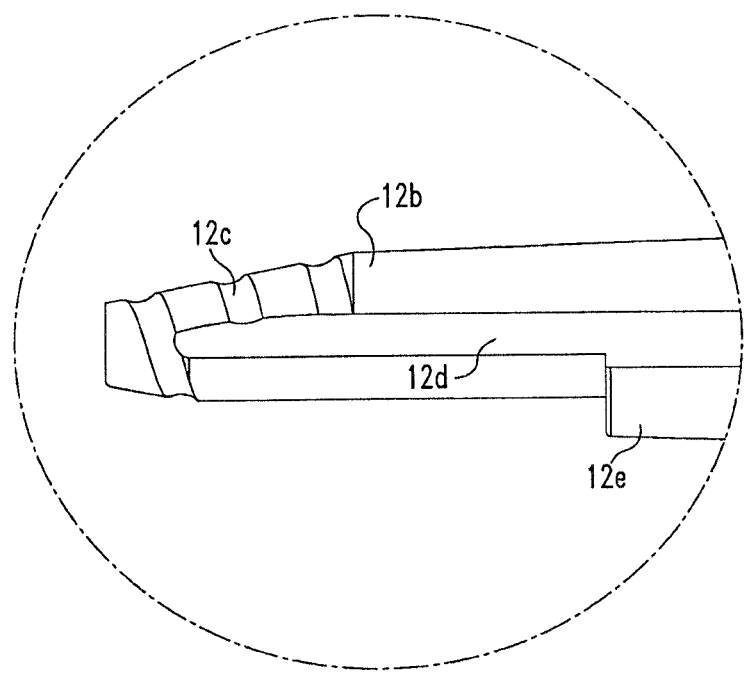
FIG. 2A shows an exploded view of the distal end of the shaft of FIG. 2.
Figure 4:
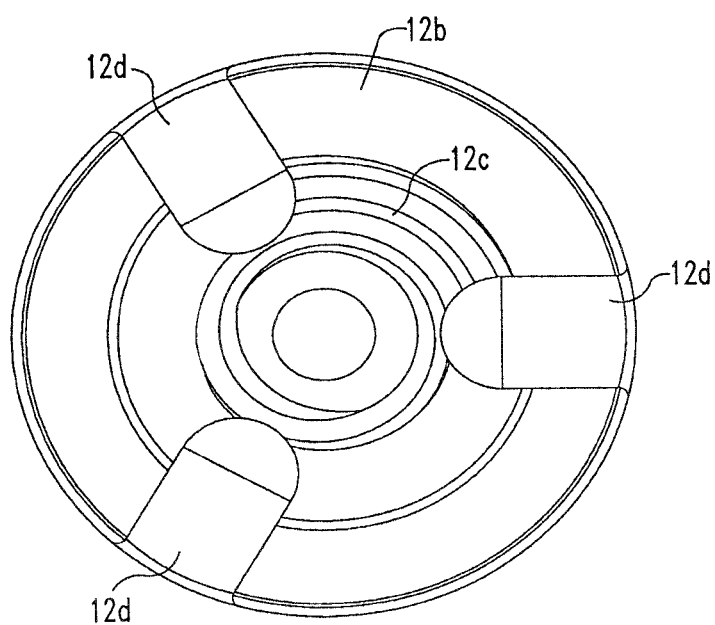
FIG. 4 shows a front view of the distal end of the shaft of FIG. 2.

The following description of the preferred embodiment(s) is merely exemplary in nature and is in no way intended to limit the disclosure, its application, or uses.

FIG. 1 shows a first embodiment of the delivery device 10 of the present disclosure. The device 10 includes a handle assembly 11 and a shaft 12 coupled to the handle assembly 11. The handle assembly 11 includes a handle 11a and a connector 11b coupled to the handle 11a. The connector 11b has a channel 11b' and an opening 11b'' to the channel 11b'. The opening 11b'' is in the shape of a "D". A proximal end 12a of the shaft 12 is disposed within the channel 11b'.

FIGS. 2, 2A, and 3-4 show the shaft 12. The shaft 12 includes a proximal end 12a and a distal end 12b. The proximal end 12a is in the shape of a "D" to match the shape of the opening 11b''. The distal end 12b includes threads 12c, grooves 12d, and a depth stop 12e. The grooves 12d extend a partial length of the shaft 12 and intersect the threads 12c. The depth stop 12e is for use with a depth stop on a screw that the device 10 is used to implant into a bone tunnel during ligament reconstruction surgery.

Figure 5:
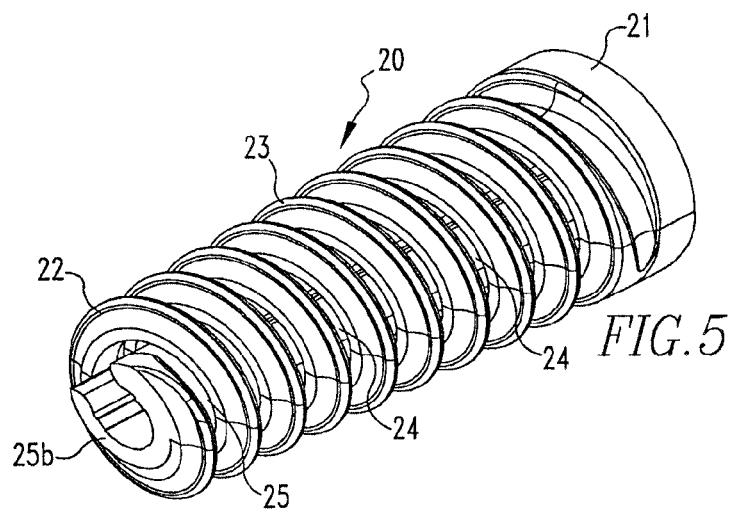
FIG. 5 shows an isometric view of the screw for use with the shaft of FIG. 2.
Figure 6:
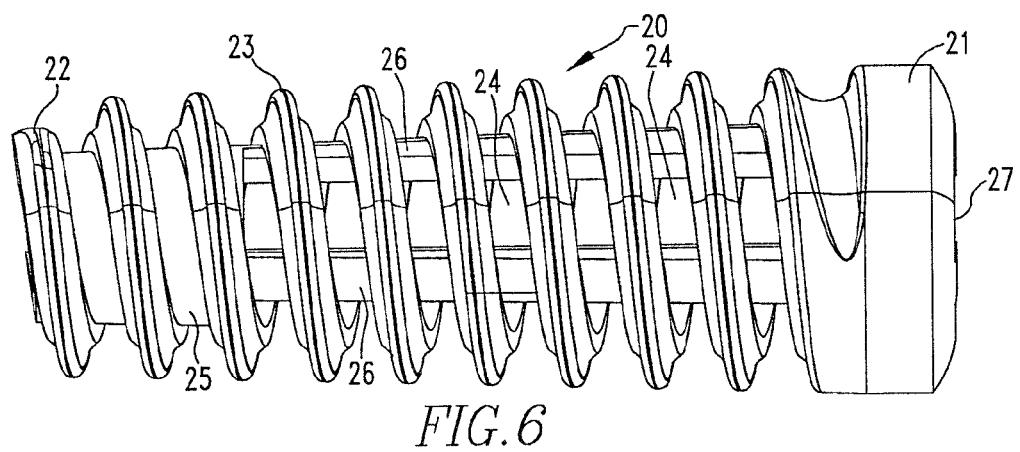
FIG. 6 shows a side view of the screw of FIG. 5.
Figure 7:
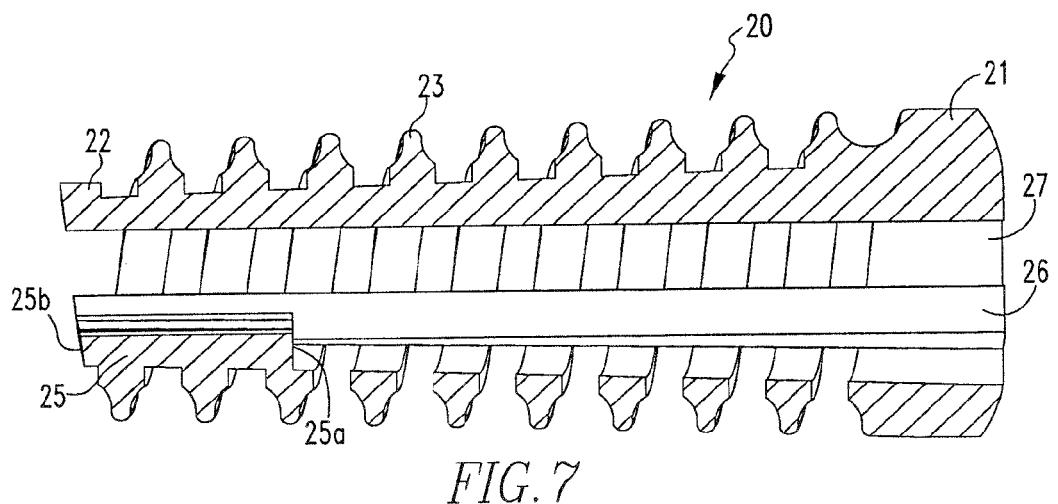
FIG. 7 shows a cross-sectional view of the screw of FIG. 6.
Figure 9A:
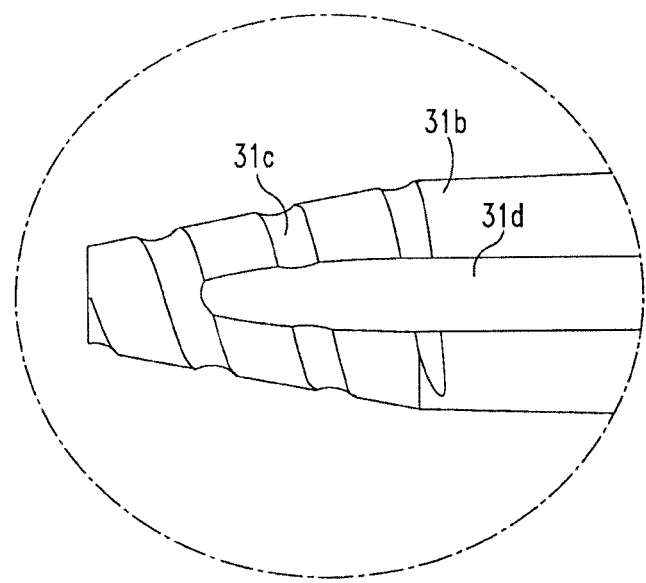
FIG. 9A shows an exploded view of the distal end of the inner member of FIG. 9.
Figure 11:
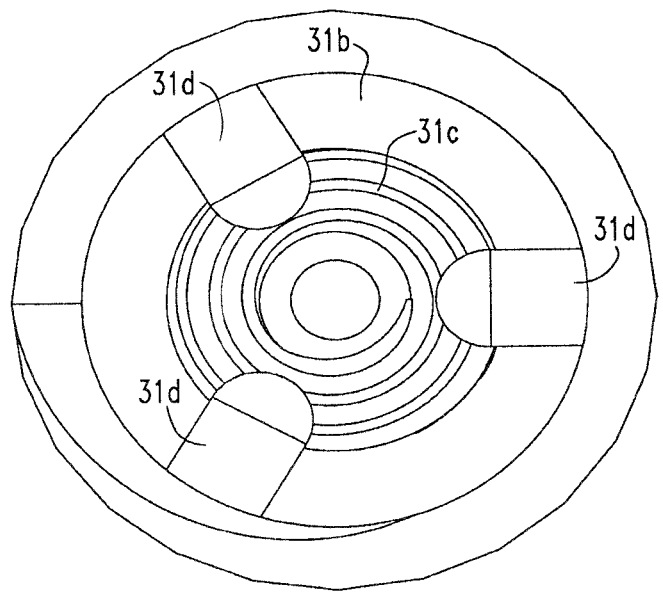
FIG. 11 shows a front view of the distal end of the inner member of FIG. 9.
Figure 16:
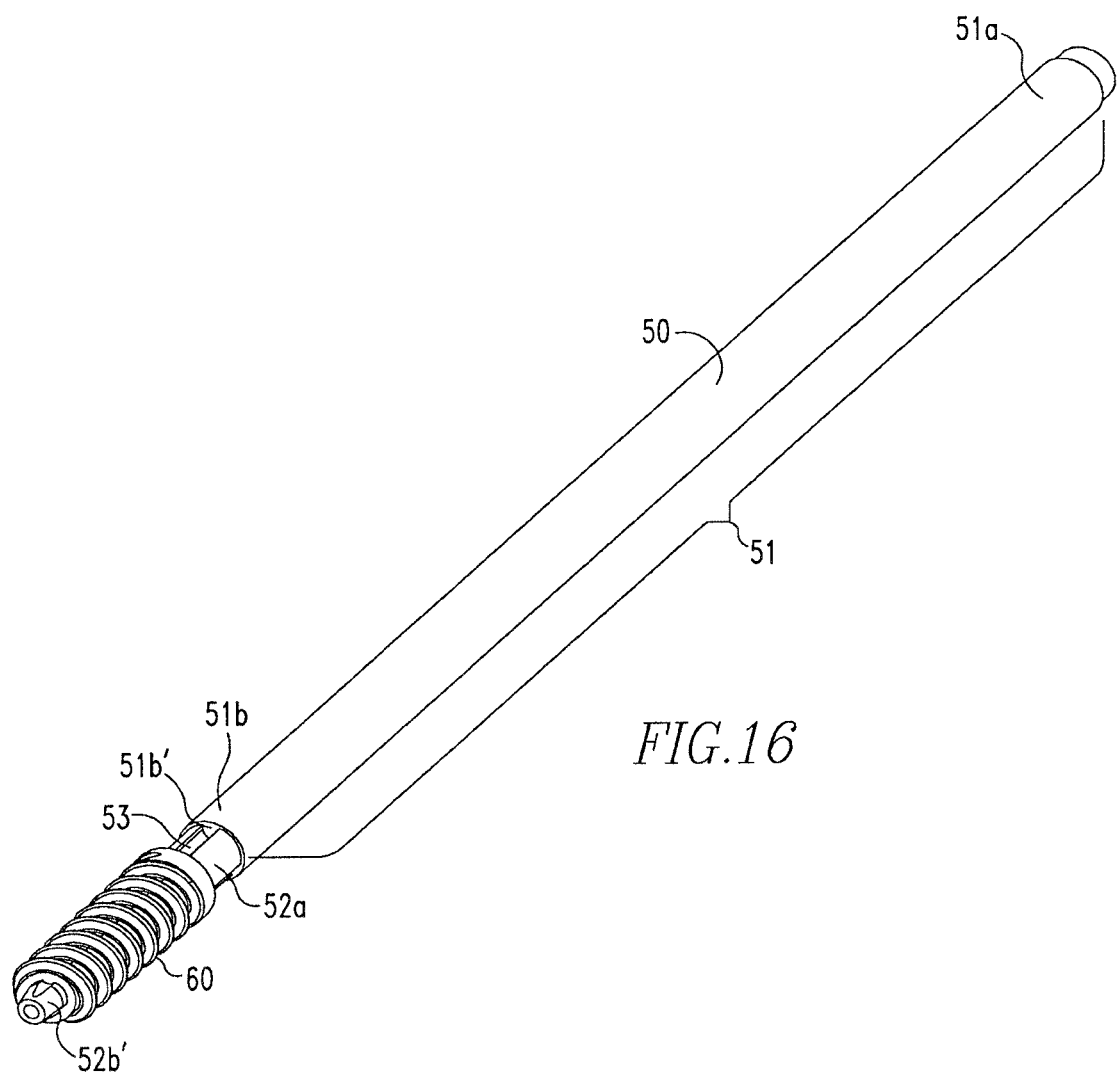
FIG. 16 shows an isometric view of a third embodiment of a shaft of the present disclosure and a screw for use with the shaft.
Figure 17:
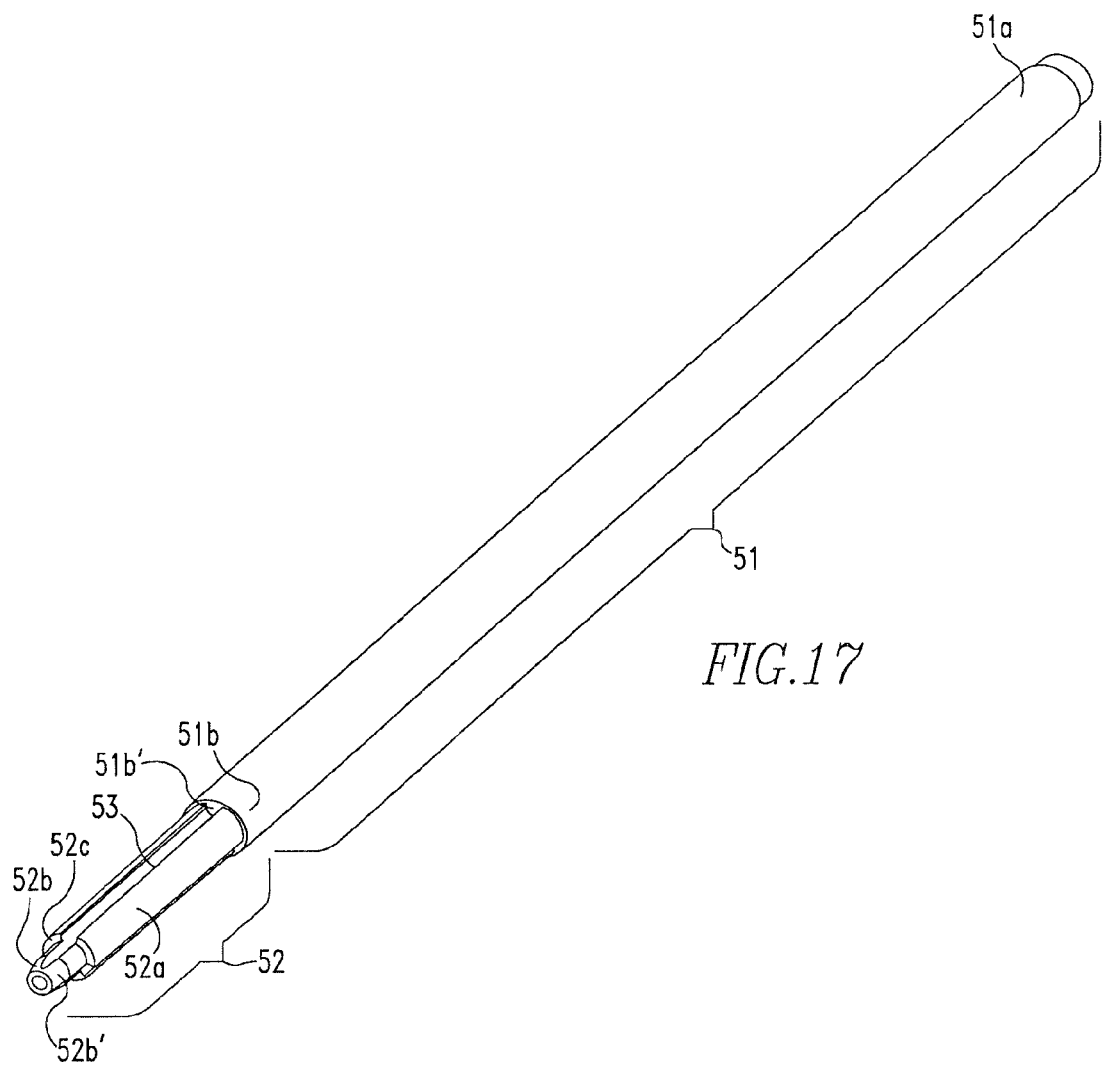
FIG. 17 shows an isometric view of the shaft of FIG. 16.
Figure 18:
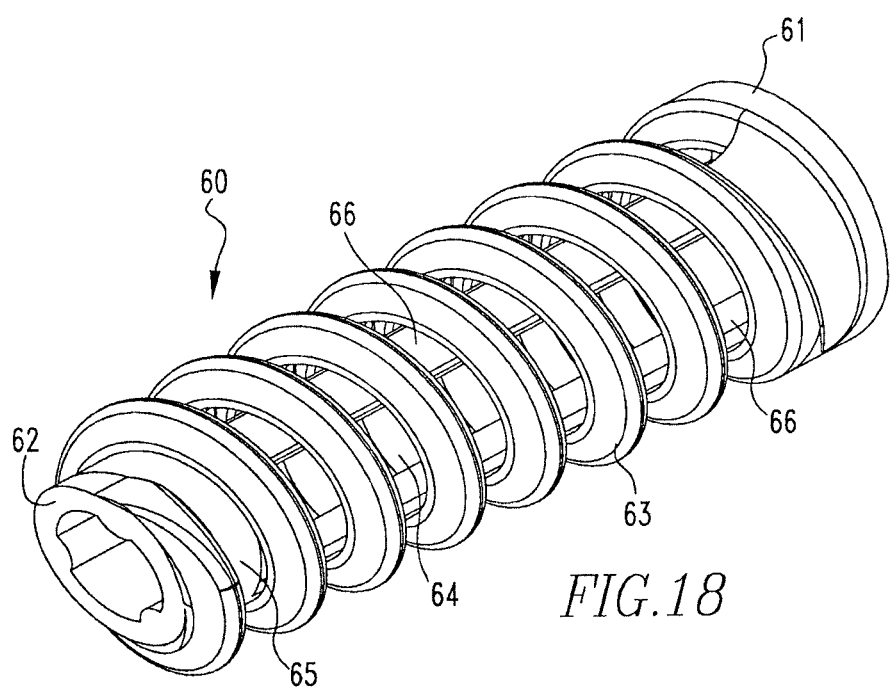
FIG. 18 shows an isometric view of the screw of FIG. 16.
Figure 19:
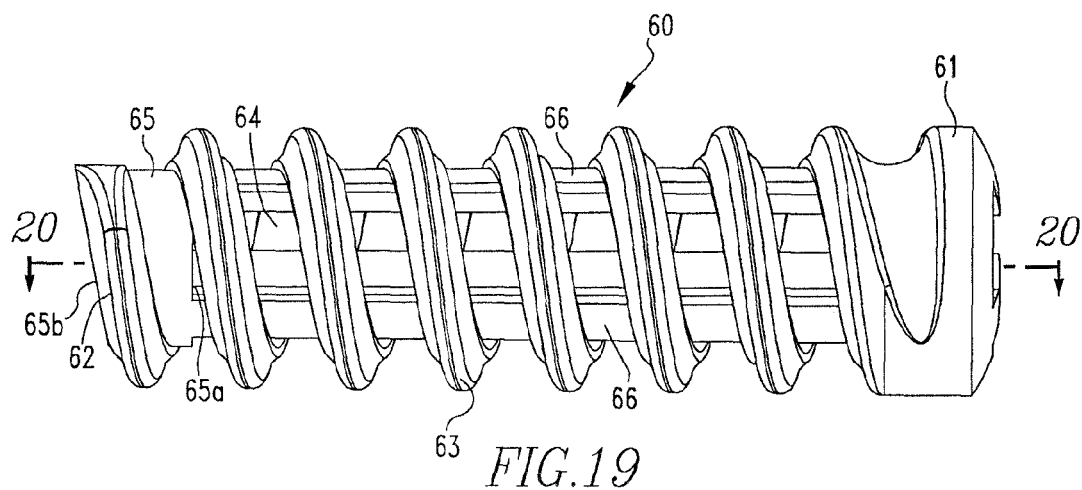
FIG. 19 shows a side view of the screw of FIG. 16.
Figure 20:
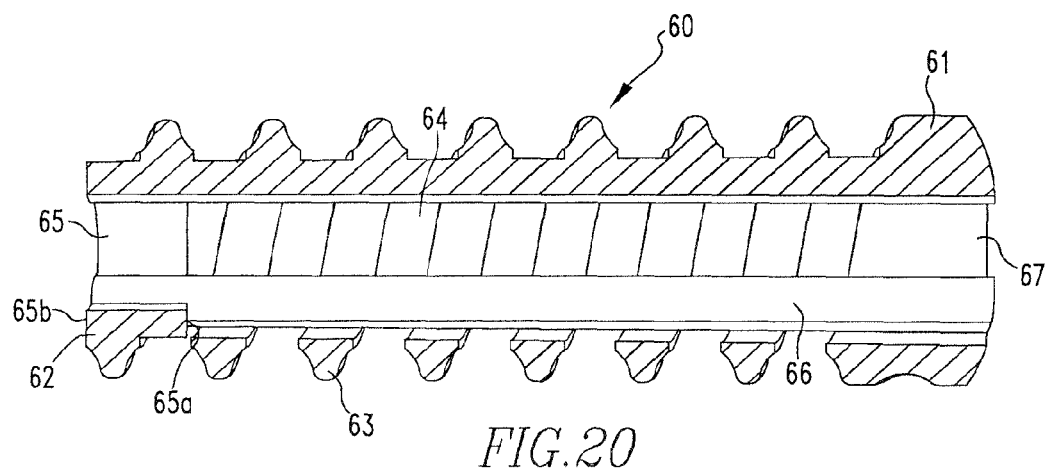
FIG. 20 shows a cross-sectional view of the screw of FIG. 19.

FIGS. 5-7 show the screw 20 for use with the delivery device 10 of the present disclosure. The screw 20 includes a proximal end 21 and a distal end 22. A majority of the screw 20 includes screw threads 23 in the form of an open helical coil, i.e. a connected series of continuous regularly spaced turns extending in a helical or spiral form substantially from the proximal end 21 to the distal end 22 with apertures 24 being defined by the space between the turns of the coil. In other words, interference screw 20 may include an open helical coil defining an internal volume, with the internal volume communicating with the region exterior to the open helical coil through the spacing between the turns of the open helical coil. The distal end 22 also includes a depth stop 25 that extends a partial length of the screw 20. The depth stop 25 includes a proximal end 25a and a distal end 25b. Additionally, a plurality of longitudinally-extending runners 26 extend along the interior of the screw threads 23.

The distal end 12b of the shaft 12 is placed within the interior of the screw 20, via the opening 27, until the proximal end 25a of the depth stop 25 engages the depth stop 12e of the shaft 12. During insertion of the shaft 12 into the screw 20, the runners 26 engage the grooves 12d and become housed within the grooves 12d. As shown in FIG. 1, the distal end 12b of the shaft 12 also includes hash marks 12f, each of which is associated with a number 12g. Once the screw 20 is placed on the shaft 12, the proximal end 21 of the screw 20 aligns with one of the hash marks/numbers 12f, thereby indicating the length of the screw 20.

FIGS. 8, 9-9A, and 10-15 show an alternative shaft 30 of the present disclosure. The shaft 30 includes an inner member 31 and an outer member 32 disposed over the inner member 31. The proximal end 31a of the inner member 31 is similar in shape to the proximal end 12a of the shaft 12. The distal end 31b of the inner member 31 includes threads 31c. Grooves 31d extend along the member 31 and intersect the threads 31c. Additionally, threads 31e are located between the proximal and distal ends 31a, 31b of the member 31. The outer member 32 includes a first section 32a and a second section 32b. The first section 32a has a larger diameter than the second section 32b. The first section 32a also includes threads 32e on an inner wall 32d of the outer member 32.

Once the outer member 32 is disposed over the inner member 31, threads 32e engage threads 31e to move the outer member 32 relative to the inner member 31. Moving the outer member 32 relative to the inner member 31 allows for more or less of the distal end 31b of the inner member 31 to be shown. Similar to the distal end 12b of the shaft 12, the distal end 31b of inner member 31 includes hash marks/numbers (not shown) that align with an end 32b' of the second section 32b, thereby indicating a length of screw 40 that will be disposed on the distal end 31b of the inner member 31. As shown in FIGS. 14 and 15, the outer member 32 is located at different positions along the length of the inner member 31 to allow for screws 40 of different lengths to be loaded on the distal end 31b of the inner member 31.

A handle assembly, similar to the handle assembly 11, is coupled to the proximal end 31a of the inner member 31. Similar to screw 20, screw 40 includes a proximal end 41 and a distal end 42. The screw 40 includes screw threads 43 in the form of an open helical coil having an interior and a plurality of longitudinally-extending runners 45 extending along the interior of the screw threads 43. Screw 40 is more fully described in United States Patent Application Publication No. 20080154314, the disclosure of which is incorporated herein by reference in its entirety. Once the outer member 32 has been moved to indicate the screw length, the screw 40 is loaded onto the distal end 31b, such that a proximal end 41 of the screw 40 engages the end 32b' and the runners 45 engage the grooves 31d and become housed within the grooves 31d.

FIGS. 16-20 show another alternative embodiment of the shaft 50 and screw 60 of the present disclosure. The shaft 50 includes a first portion 51 including a proximal end 51a and a distal end 51b and a second portion 52 including a first area 52a and a second area 52b. The proximal end 51a is configured to be coupled to a handle assembly, similar to the handle assembly 11. However, other handle assemblies may be used. The first area 52a has a smaller diameter than the first portion 51, such that a first depth stop 51b' exists at the distal end 51b of the first portion 51. The second area 52b has a smaller diameter than the first area 52a such that a second depth stop 52c exists between the first area 52a and the second area 52b. An end 52b' of the second area 52b is tapered to allow for easier insertion of the anchor 60 into a bone during ligament reconstruction surgery, as will be further described below. The second portion 52 also includes grooves 53 extending between the first and second areas 52a, 52b. For the purposes of this disclosure, there are three grooves 53. However, the second portion 52 may include a higher or lower number of grooves 53.

Similar to screw 20 shown in FIGS. 5-7, screw 60 includes a proximal end 61 and a distal end 62. A majority of the screw 60 includes screw threads 63 in the form of an open helical coil, i.e. a connected series of continuous regularly spaced turns extending in a helical or spiral form substantially from the proximal end 61 to the distal end 62 with apertures 64 being defined by the space between the turns of the coil. In other words, interference screw 60 may include an open helical coil defining an internal volume, with the internal volume communicating with the region exterior to the open helical coil through the spacing between the turns of the open helical coil. The distal end 62 also includes a depth stop 65 that extends a partial length of the screw 60. The depth stop 65 includes a proximal end 65a and a distal end 65b. Unlike the open depth stop 25 of screw 20 most clearly shown in FIG. 5, the depth stop 65 of screw 60 is a closed depth stop, most clearly shown in FIG. 18. Additionally, a plurality of longitudinally-extending runners 66 extend along the interior of the screw threads 63.

The second portion 52 of the shaft 50 is placed within the interior of the screw 60, via the opening 67, until the proximal end 65a of the depth stop 65 engages the second depth stop 52c of the shaft 50. During insertion of the shaft 50 into the screw 60, the runners 66 engage the grooves 53 and become housed within the grooves 53. The screws 60 may be of a variety of lengths. For example, a screw 60 may be of such length that its proximal end 61 would engage the first depth stop 51b'.

As described above, during ligament reconstruction surgery, the end of the graft ligament is placed in the bone tunnel and then the interference screw 20,40,60 is advanced into the bone tunnel via the use of shafts 12,30,50 so that the interference screw 20,40,60 extends parallel to the bone tunnel and simultaneously engages both the graft ligament and the side wall of the bone tunnel. The screws 20,40,60 may be used in either the femoral or tibial tunnels. Methods of ligament reconstruction via use of the screws 20,40,60 is further shown in the '314 publication shown above.

Figure 21:
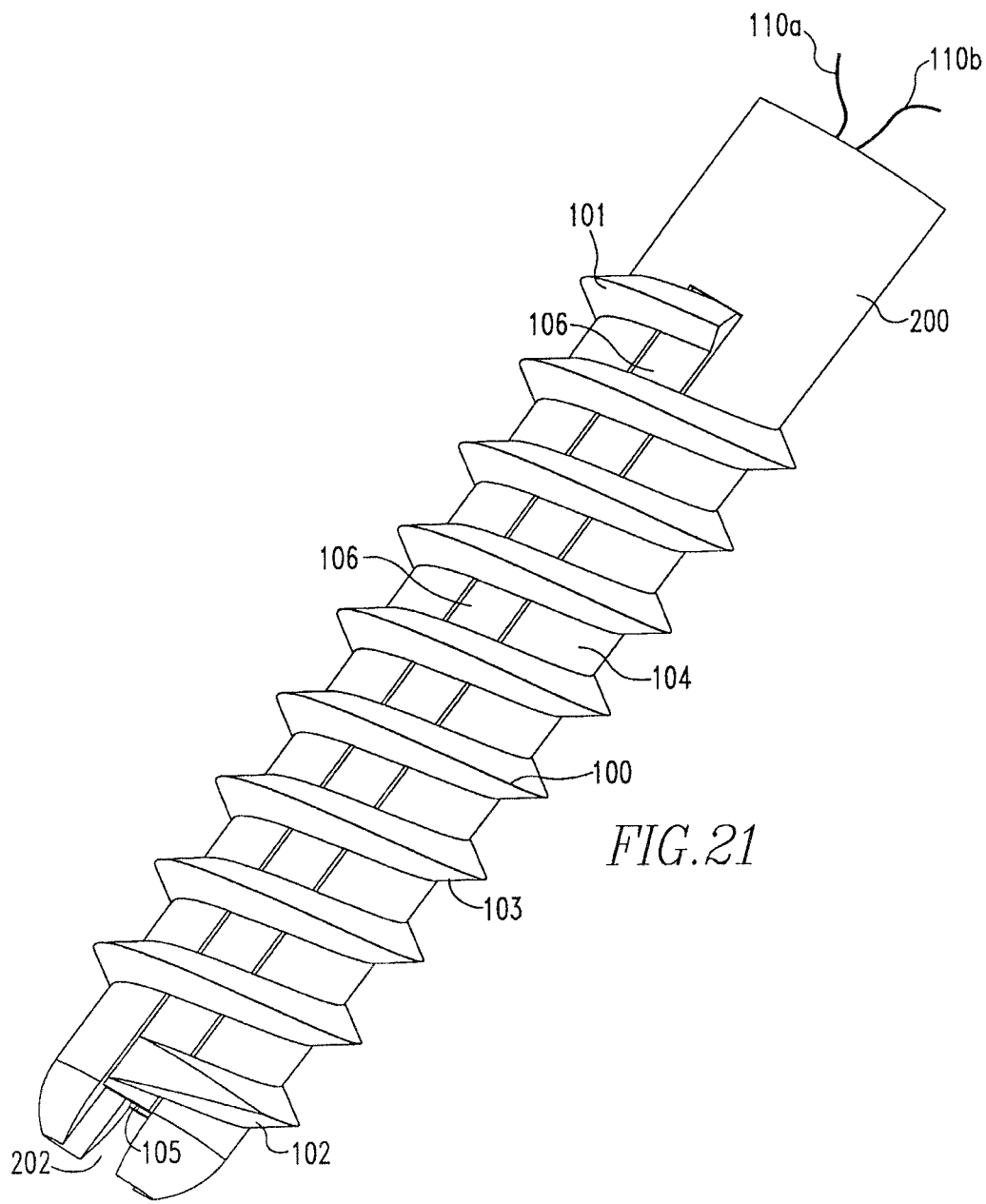
FIG. 21 shows an isometric view of a fourth embodiment of a shaft of the present disclosure and a screw for use with the shaft.
Figure 22:
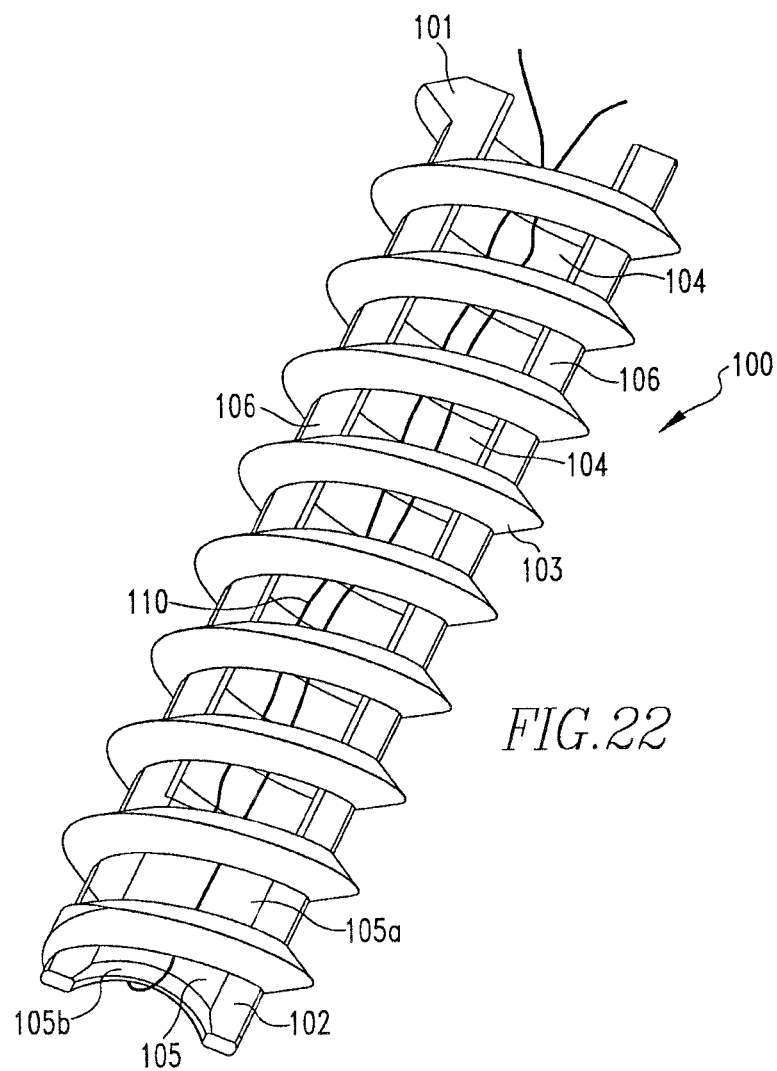
FIG. 22 shows an isometric view of the screw of FIG. 21.

FIGS. 21-23 show yet another alternative embodiment of the screw 100 and the delivery device 200 of the present disclosure. The screw 100 includes a proximal end 101 and a distal end 102. A majority of the screw 100 includes screw threads 103 in the form of an open helical coil, i.e. a connected series of continuous regularly spaced turns extending in a helical or spiral form substantially from the proximal end 101 to the distal end 102 with apertures 104 being defined by the space between the turns of the coil. In other words, interference screw 100 may include an open helical coil defining an internal volume, with the internal volume communicating with the region exterior to the open helical coil through the spacing between the turns of the open helical coil. The distal end 102 also includes a suture bridge 105 that extends a partial length of the screw 100. The suture bridge 105 includes a proximal end 105*a* and a distal end 105*b*. The distal end 105*b* includes a concave shape. A flexible member 110, such as a suture, is housed within the screw 100, such that the suture 110 extends around the distal end 105*b* of the bridge 105. Additionally, longitudinally-extending runners 106 extend from the suture bridge 105 and along the interior of the screw threads 103. For the purposes of this disclosure, there are two longitudinally extending runners 106. However, more or less than two runners are within the scope of this disclosure.

The delivery device 200 includes a distal end 201 having a slot 202 and grooves 203 extending from the slot 202 on each side of the device 200. As shown in FIG. 21, the screw 100 is located on the distal end 201 such that the suture bridge 105 is housed within the slot 202 and the runners 106 are housed within the grooves 203. The delivery device 200 is cannulated, such that when the screw 100 is located on the device 200, the suture ends 110*a*,110*b* extend through the cannulation 204.

FIGS. 24-26 show a screw 300 similar to screw 100. However, screw 300 additionally includes a pointed tip 311 located on the distal end 302. The tip 311 includes a through hole 312. The hole 312 helps in locating the suture 110 within the interior of the screw 300. As shown in FIG. 24, the screw 300 is located on the distal end 201 of delivery device 200 such that the suture bridge 305 is housed within the slot 202 and the runners 306 are housed within the grooves 203. As stated above, the delivery device 200 is cannulated, such that when the screw 300 is located on the device 200, the suture ends 110*a*,110*b* extend through the cannulation 204, as shown in FIG. 24.

For clarity purposes, only the distal end 201 of the device 200 is shown. However, the device 200 would include a proximal end, similar to the devices above, which may be coupled to a handle assembly, similar to handle assembly 11 above. The screws 100,300 are used in the repair of soft tissue, specifically to re-attach tissue to bone. One example of this repair is when the screw 100,300 is delivered into bone via the use of device 200, the device 200 is removed from screw 100,300, the tissue is placed on the bone to be adjacent the screw 100,300, the suture ends 110*a*,110*b* are pulled through the tissue, and then the suture ends 110*a*,110*b* are tied. A hole may be made in the bone prior to insertion of the screw 100,300 into the bone. However, screw 300 may be inserted into bone without first making a hole in the bone. In this case, the pointed tip 311 is used to start insertion of the screw 300 into the bone and then rotary motion may be used to complete insertion of the screw 300 into the bone. Other methods of tissue repair via use of these screws and delivery device may also be used.

The distal end 201 of the delivery device 200 may be shaped so as to be able to pierce bone and provide entry of the screw 100 into bone, thereby serving a purpose similar to the pointed tip 311 of screw 300. The distal end 201 may have an awl shape, may be pointed, or have some other shape that would allow for initiation of screw 100 insertion into the bone without having to use a separate tool.

Figure 27:
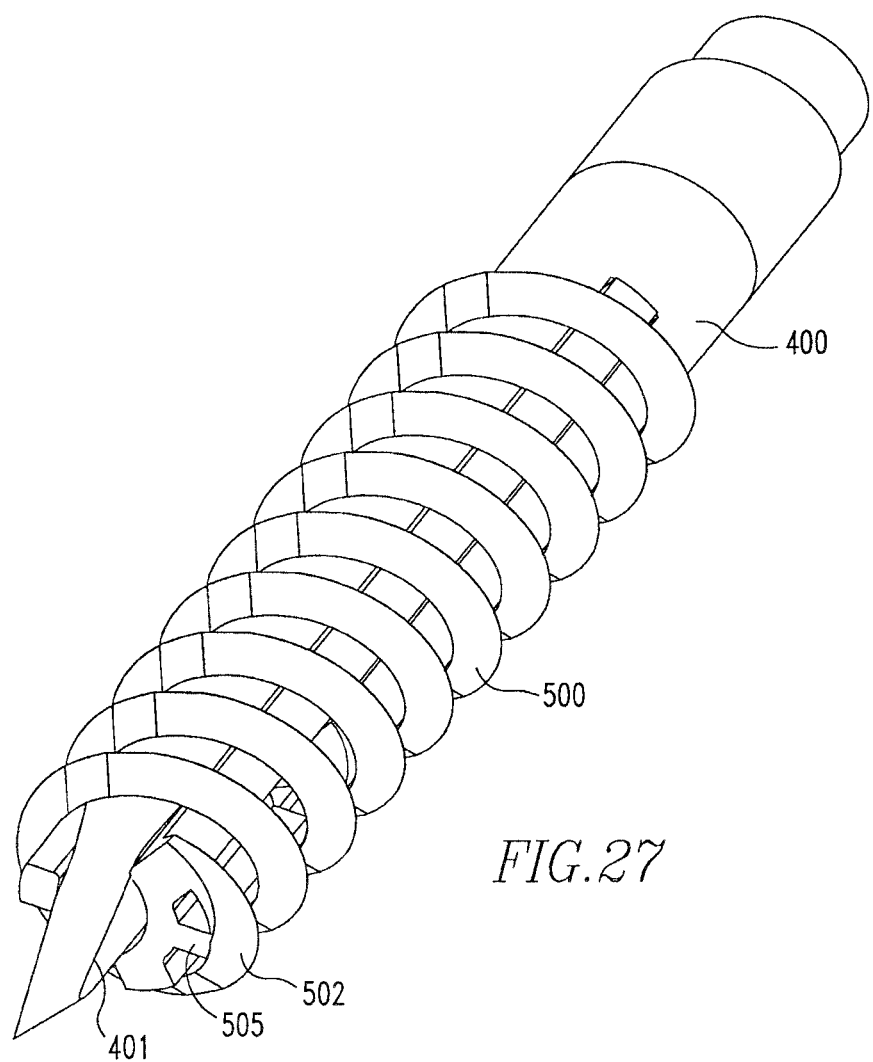
FIG. 27 shows an isometric view of a fifth embodiment of a shaft of the present disclosure and a screw for use with the shaft.

FIG. 27 shows an alternative embodiment of the delivery device 200 and the screw 100. The delivery device 400 of FIG. 27 includes a distal end 401 in the form of a single pointed tip. The tip 401 extends beyond the distal end 502 of the screw 500. The screw 500 is different from screw 100 in the sense that the suture bridge 505 is not centrally located on the screw 500. Rather, the suture bridge 505 is located laterally or on a side of the screw 500. Having the suture bridge 505 located laterally allows the delivery device 400 to maintain a solid centrally located tip 401, rather than the split distal end 201 of delivery device 200. Similar to screw 100, suture would extend around the bridge 505 and ends of the suture would extend through a cannulation of the delivery device 400. Similar to the awl shaped distal end 201 discussed above, the distal end 401 of delivery device 400 also allows for initiation of screw 500 insertion into the bone without having to use a separate tool.

Figure 28:
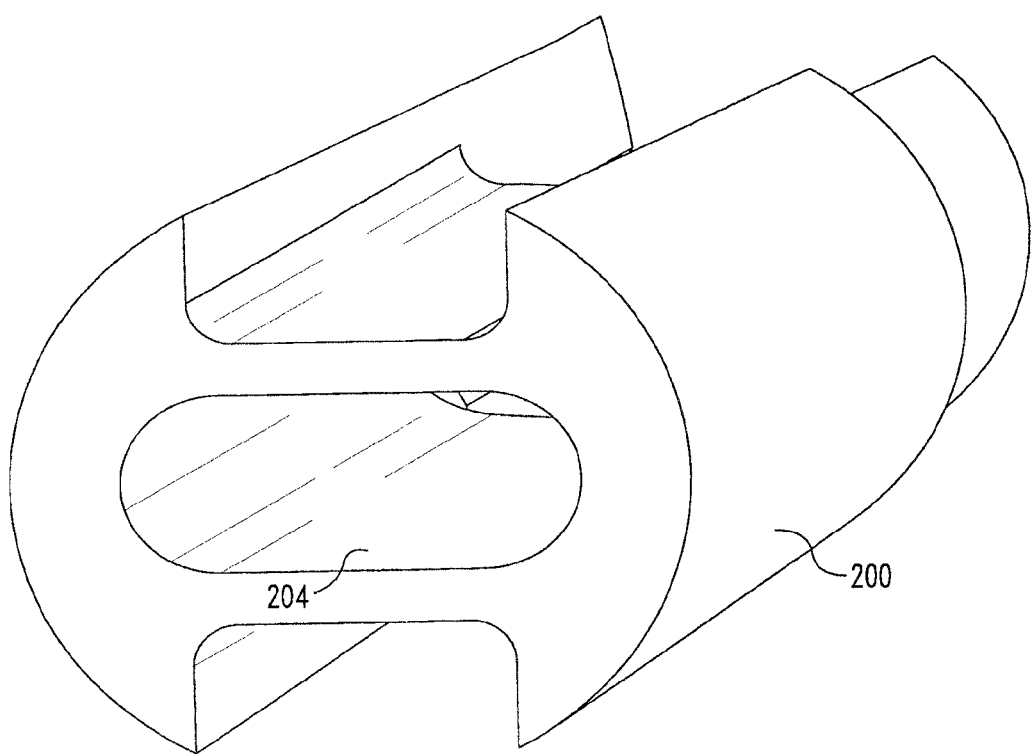
FIG. 28 shows a cross-sectional view of the shaft of FIG. 21.
Figure 29:
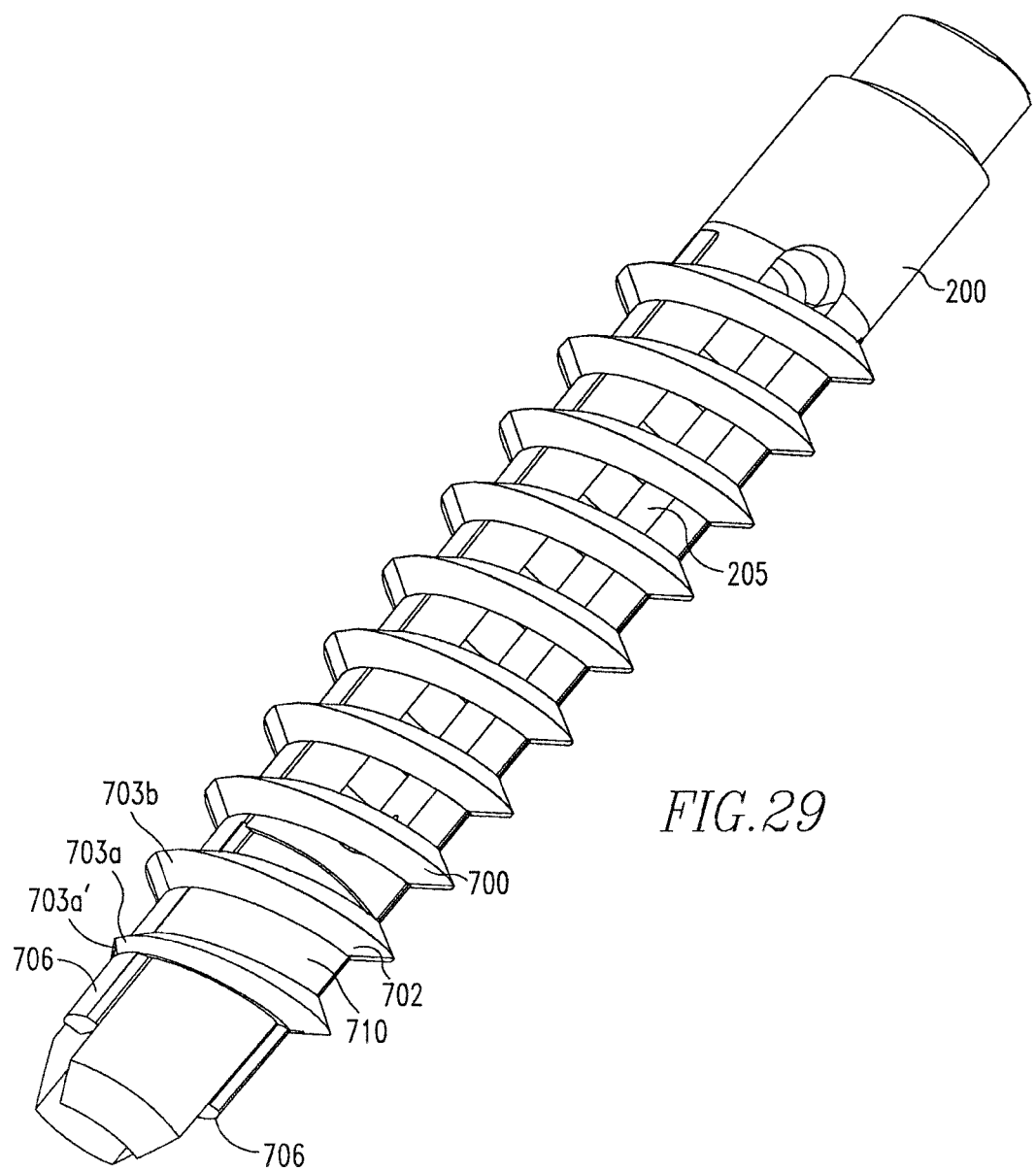
FIG. 29 shows an isometric view of a sixth embodiment of a shaft of the present disclosure and a screw for use with the shaft.
Figure 30:
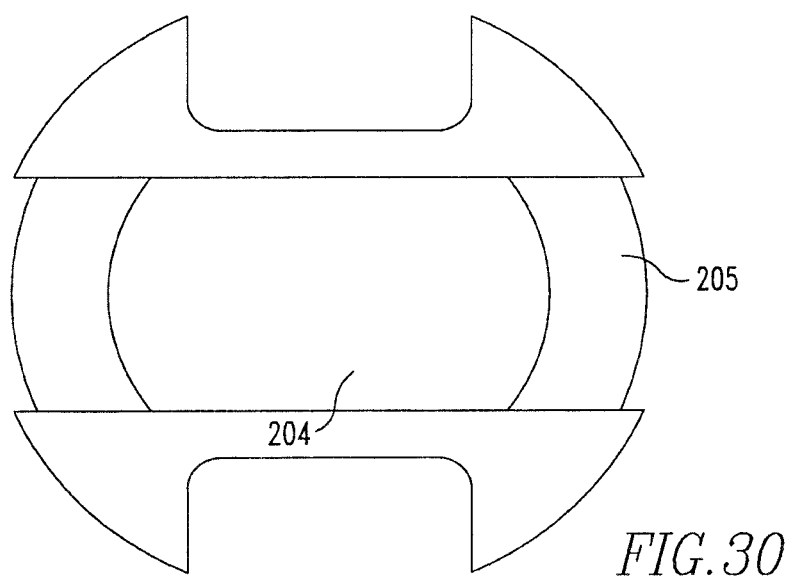
FIG. 30 shows a cross sectional view of the shaft of FIG. 29.

As shown in FIG. 24, the cannulation 204 of the delivery device 200 is oval-shaped. FIG. 28 shows a cross-sectional view of delivery device 200, further evidencing the oval-shaped cannulation 204. In order to accommodate the full suture load inside of the cannulation 204, a non-circular shape, including, but not limited to, an oval shape or a rectangular shape, is used. FIGS. 29 and 30 show an embodiment of the delivery device 200 whereby a longitudinal slot cut 205 is made completely through the device 200. Having the slot cut 205 also serves the purpose of accommodating a full suture load inside of the cannulation 204. The slot cut 205 is in an elongated oval shape form for the purposes of FIG. 29. However, the slot cut 205 could be of any shape, including, without limitation, rectangular shaped. The delivery device 200 is also tapered to be awl shaped, as described above, so as to be able to pierce bone and provide entry of the screw 700 into bone.

FIG. 29 also shows a screw 700 having a distal end 702 with a web 710 located between thread 703*a* and thread 703*b*. During insertion of the screw 700 into bone, thread 703*a* is the first thread to enter the bone. The starting point 703*a*' of thread 703*a* is engaged with the runner 706. This small engagement area requires the thread 703*a* to very rapidly transition to the full threads proximal to thread 703*a*, such as thread 703*b*. Without a web 710 between threads 703*a* and 703*b*, the starting point 703*a*' of thread 703*a* may disengage from runner 706. With the starting point 703*a*' disengaged from the runner 706, further rotation of the screw 700 may cause further disengagement of thread 703*a* and threads proximal to thread 703*a*, such as thread 703*b*, to disengage from runners 706. Therefore, web 710 provides the support needed to substantially reduce the possibility of the threads disengaging from the runners 706, beginning with the starting point 703*a*' of thread 703*a*. For the purposes of this disclosure, the web 710 extends between threads 703*a* and 703*b* and spans about 180 degrees circumferentially around the screw 700 or from one runner 706 to the other runner 706. It is within the scope of this disclosure for webs, similar to web 710, to exist between the threads proximal to thread 703*b*. It is also within the scope of this disclosure for web 710 to span more or less than 180 degrees circumferentially around the screw 700. Furthermore, for the purposes of FIG. 29, the web 710 is solid. However, it is within the scope of this disclosure that the web 710 could be non-solid, including, without limitation, a perforated web.

Figure 31:
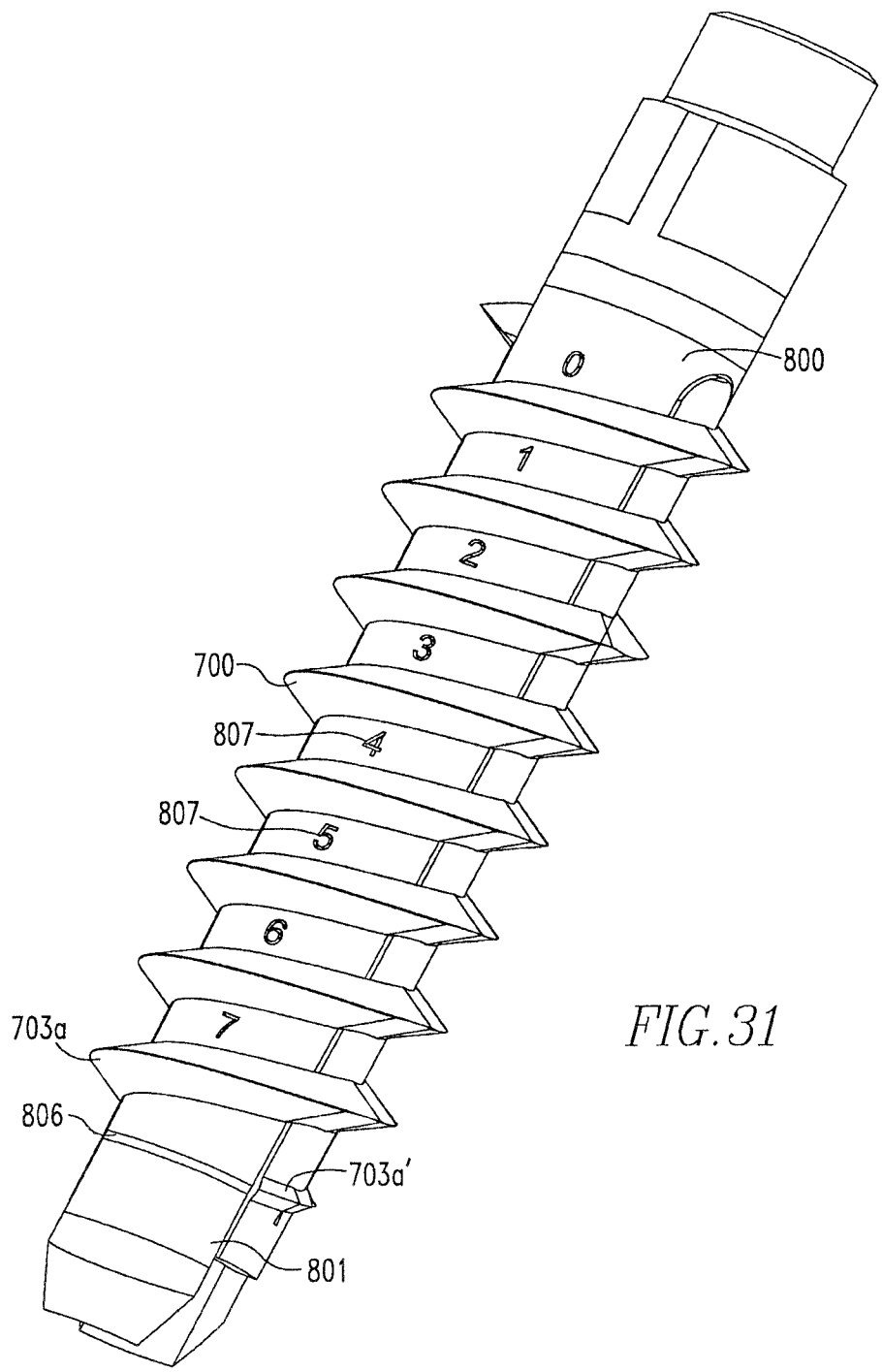
FIG. 31 shows an isometric view of a seventh embodiment of a shaft of the present disclosure and a screw for use with the shaft.

FIG. 31 shows a delivery device, such as delivery device 800, including markings 806,807. The markings 806,807 provide feedback to the surgeon as to the insertion progress of the screw 700. The distal end 801 of the delivery device 800 is tapered to be awl shaped, as described above, so as to be able to pierce bone and provide entry of the screw 700 into bone. Marking 806 is located in-line with the starting point 703*a*' of thread 703*a* to provide visual feedback to the surgeon during insertion of the screw 700 into bone. For example, the surgeon axially inserts the distal end 801 of the device 800 into bone up to marking 806. Subsequently, the surgeon rotates the device 800 to insert the screw 700 into the bone. During screw 700 insertion, markings 807 provide feedback on screw 800 insertion progress. As shown in FIG. 31, markings 807 are numbers that create a countdown sequence. However, types of markings, other than numbers, could be used. While screw 700 is shown as being used with delivery device 800, screw 100 could also be used with device 800.

The handle 11a of handle assembly 11 is made from plastic, however, other non-metal and metal materials may also be used. The shape and size of handle 11a may be any shape and size necessary to help facilitate insertion of the screw 20 into bone. The coupler 11b is made from a metal material, such as stainless steel or titanium, but may be made from other metal and non-metal materials that are strong enough to withstand the forces applied during surgery. The coupler 11b is press-fit to the handle 11a, but may be coupled to the handle 11a in any other manner known to those of skill in the art. The size and shape of the coupler 11b may be any size and shape necessary to help facilitate insertion of the screw 20 into bone. The channel 11b' may be any length necessary and the opening 11b" may be any shape necessary to facilitate coupling of the shaft 12 to the coupler 11b.

The shaft 12 is made from a metal material, such as stainless steel and titanium, however, other metal and non-metal materials that would withstand the forces applied during surgery may be used. The diameter of the shaft 12 may vary. The proximal end 12a of the shaft 12 may be any shape necessary to facilitate insertion of the end 12a through opening 11b' and into channel 11b'. The number of threads 12e and grooves 12d may vary and the lengths of the grooves 12d may also vary. The location of depth stop 12e may also vary based on the diameter of the shaft 12 and the diameter of the screw 20 that is used. The grooves 12d, depth stop 12e, and threads 12c may be formed by any method known to one of skill in the art.

The screw 20 is made from a polymer material via a molding method. However, other material, which would allow the screw 20 to withstand forces applied during surgery, and other methods of making may be used. The depth stop 25 is open ended and doesn't extend the entire inner diameter of the screw 20. The amount of screw inner diameter that the depth stop 25 covers may vary and the length of the depth stop 25 may vary based on the diameter of the screw. The number and length of the runners 26 may also vary. Once the screw 20 is located on the shaft 12, the distal end 12b of the shaft 12 extends from the distal end 22 of the screw 20. During insertion of the screw 20 into bone, the threads 12c create threads in the bone, thereby creating a seat for the screw threads 23, as described more fully in the '314 publication. The amount of the distal end 12b of the shaft 12 that extends from the distal end 22 of the screw 20 may vary.

The diameters of the first and second sections 32a,32b of outer member 32 may vary and the number of threads 32c may also vary. The number of threads 31c,31e and grooves 31d may vary and the lengths of the grooves 31d may also vary. The inner and outer members 31,32 are made from a metal material, such as stainless steel and titanium, and via a method known to one of skill in the art. However, other materials may also be used. The screw 40 is made from a polymer material via a molding method. However, other material and methods of making may be used. The number and length of the runners 45 may also vary. Once the screw 40 is located on the shaft 30, the distal end 31b of the shaft 30 extends from the distal end 42 of the screw 40. During insertion of the screw 40 into bone, the threads 31c create threads in the bone, thereby creating a seat for the screw threads 43, as described more fully in the '314 publication. The amount of the distal end 31b of the shaft 30 extending from the screw 40 may vary.

The shaft 50 is made from a metal material, such as stainless steel or titanium, but may be made from another metal material or a non-metal material that is strong enough to withstand the force applied to the shaft 50 during surgery. The shaft 50 may be made via a method known to one of skill in the art. The diameters of the first and second portions 51,52 may vary along with the number and lengths of the grooves 53 and the locations of the depth stops 52c,51b' may vary based on the diameter of the screw 60 or other factors. Rather than being tapered, the end 52b' may be designed in another manner to allow easier insertion of the screw 60 into bone. The screw 60 is made from a polymer material via a molding method. However, other material, which would allow the screw to withstand the forces applied during surgery, and other methods of making may be used. The number and length of the runners 66 may also vary. Once the screw 60 is located on the shaft 50, the second portion 52 of the shaft 50 extends from the distal end 62 of the screw 60. The amount of the second portion 52 extending from the screw 60 may vary. Additionally, the length of the depth stop 65 may also vary based on the diameter of the screw 60 or other factors.

The delivery device 200 is made from a metal material, such as stainless steel or titanium, but may be made from a non-metal material that is strong enough to withstand the forces applied to the device 200 during surgery. The delivery device 200 is made via a method known to one of skill in the art. The screws 100,300 are made from a polymer material and via a molding process, however, other material, which would allow the screw to withstand the forces applied during surgery, and other processes known to one of skill in the art may be used. The suture bridge 105 may have a distal end 105b having a shape other than concave and the length of the suture bridge 105, the slot 202, and the grooves 203 may vary. The size and the shape of the hole 312 may vary.

As various modifications could be made to the exemplary embodiments, as described above with reference to the corresponding illustrations, without departing from the scope of the disclosure, it is intended that all matter contained in the foregoing description and shown in the accompanying drawings shall be interpreted as illustrative rather than limiting. Thus, the breadth and scope of the present disclosure should not be limited by any of the above-described exemplary embodiments, but should be defined only in accordance with the following claims appended hereto and their equivalents.

The invention claimed is:
1. A delivery device for an interference screw comprising:
   a handle;
   a connector coupled to the handle, the connector including a channel and an opening to the channel;
   a shaft coupled to the connector including a proximal end and a distal end, the proximal end having an increased diameter at a shoulder portion formed between the proximal and distal ends, the distal end comprising a tapered threaded portion and at least one groove intersecting the threads of the threaded portion, the at least one groove for housing a portion of an interference screw; and
   a depth stop defined by the shoulder portion for engaging a corresponding depth stop on the interference screw;
   wherein the shoulder portion extends for less than a full extent around a circumference of the shaft.

2. The delivery device of claim 1, wherein the shaft comprises depth markings along a length of a surface of the shaft.

3. The delivery device of claim 1, wherein the opening of the connector is in a shape of a "D".

4. The delivery device of claim 1, wherein the proximal end of the shaft is disposed within the channel of the connector.

5. The delivery device of claim 1, wherein a diameter of the handle is selected to be larger than a diameter of the shaft.

6. The delivery device of claim 1, wherein the handle is comprised of plastic, and the connector and the shaft are comprised of metal.

7. The delivery device of claim 1, wherein the proximal end of the shaft has a shape configured to match a shape of the opening of the connector.

* * * * *